(12) United States Patent
Schacht et al.

(10) Patent No.: US 8,246,980 B2
(45) Date of Patent: *Aug. 21, 2012

(54) TRANSDERMAL DELIVERY SYSTEM

(75) Inventors: Dietrich Wilhelm Schacht, Köln (DE); Mike Hannay, Wachtberg-Villiprott (DE); Hans-Michael Wolff, Monheim (DE)

(73) Assignee: UCB Pharma GmbH, Monheim (DE)

( * ) Notice: Subject to any disclaimer, the term of this patent is extended or adjusted under 35 U.S.C. 154(b) by 853 days.

This patent is subject to a terminal disclaimer.

(21) Appl. No.: 10/627,990

(22) Filed: Jul. 28, 2003

(65) Prior Publication Data

US 2004/0081683 A1    Apr. 29, 2004

Related U.S. Application Data

(60) Provisional application No. 60/451,715, filed on Mar. 5, 2003.

(30) Foreign Application Priority Data

Jul. 30, 2002 (EP) ................................. 02016864

(51) Int. Cl.
*A61K 9/70* (2006.01)
*A61K 9/14* (2006.01)
*A01N 43/40* (2006.01)

(52) U.S. Cl. .................... 424/449; 424/484; 514/277

(58) Field of Classification Search .................. 424/443, 424/448, 449, 484; 514/277
See application file for complete search history.

(56) References Cited

U.S. PATENT DOCUMENTS

| | | | | |
|---|---|---|---|---|
| 3,797,494 A | * | 3/1974 | Zaffaroni | 424/434 |
| 4,588,580 A | * | 5/1986 | Gale et al. | 424/449 |
| 4,915,950 A | | 4/1990 | Miranda et al. | 424/449 |
| 4,973,468 A | | 11/1990 | Chiang et al. | 424/449 |
| 5,069,909 A | | 12/1991 | Sharma et al. | 424/449 |
| 5,091,186 A | | 2/1992 | Miranda et al. | 424/448 |
| 5,124,157 A | | 6/1992 | Colley et al. | 424/448 |
| 5,147,916 A | | 9/1992 | Sweet | 524/266 |
| 5,177,112 A | | 1/1993 | Horn | 514/65 |
| 5,217,718 A | * | 6/1993 | Colley et al. | 424/449 |
| 5,225,198 A | | 7/1993 | Sharma et al. | 424/443 |
| 5,232,702 A | * | 8/1993 | Pfister et al. | 424/448 |
| 5,234,690 A | | 8/1993 | Chiang et al. | 424/448 |
| 5,246,997 A | | 9/1993 | Sweet | 524/266 |
| 5,252,334 A | | 10/1993 | Chiang et al. | 424/448 |
| 5,252,335 A | | 10/1993 | Chiang | 424/449 |
| 5,271,940 A | | 12/1993 | Cleary et al. | 424/448 |
| 5,273,755 A | | 12/1993 | Venkatraman et al. | 424/448 |
| 5,273,756 A | | 12/1993 | Fallon et al. | 424/448 |
| 5,273,757 A | | 12/1993 | Jaeger et al. | 424/448 |
| 5,308,625 A | | 5/1994 | Wong et al. | 424/449 |
| 5,382,596 A | | 1/1995 | Sleevi et al. | 514/459 |
| 5,393,529 A | | 2/1995 | Hoffman et al. | 424/445 |
| 5,456,745 A | | 10/1995 | Roreger et al. | 106/128 |
| 5,500,222 A | * | 3/1996 | Lee et al. | 424/448 |
| 5,554,381 A | | 9/1996 | Roos et al. | 424/449 |
| 5,601,839 A | | 2/1997 | Quan et al. | |
| 5,670,164 A | | 9/1997 | Meconi et al. | 424/448 |
| 5,676,968 A | * | 10/1997 | Lipp et al. | 424/448 |
| 5,688,524 A | | 11/1997 | Hsu et al. | 424/449 |
| 5,733,571 A | | 3/1998 | Sackler | 424/449 |
| 5,771,890 A | | 6/1998 | Tamada | 128/635 |
| 5,788,983 A | * | 8/1998 | Chien et al. | 424/449 |
| 5,807,570 A | | 9/1998 | Chen et al. | 424/449 |
| 5,834,010 A | | 11/1998 | Quan et al. | |
| 5,840,336 A | | 11/1998 | Hsu et al. | 424/484 |
| 5,876,746 A | | 3/1999 | Jona et al. | 424/449 |
| 5,879,701 A | | 3/1999 | Aduett et al. | 424/448 |
| 5,891,461 A | | 4/1999 | Jona et al. | 424/449 |
| 5,902,603 A | | 5/1999 | Chen et al. | 424/449 |
| 5,906,830 A | | 5/1999 | Farinas et al. | 424/448 |
| 5,932,240 A | * | 8/1999 | D'Angelo et al. | 424/449 |
| 5,980,932 A | | 11/1999 | Chiang et al. | 424/448 |
| 6,024,974 A | | 2/2000 | Li | 424/448 |
| 6,024,976 A | | 2/2000 | Miranda et al. | 424/449 |
| 6,063,398 A | | 5/2000 | Gueret | 424/443 |
| 6,218,421 B1 | | 4/2001 | King | 514/421 |
| 6,299,900 B1 | | 10/2001 | Reed et al. | 424/449 |
| 6,316,022 B1 | | 11/2001 | Mantelle et al. | 424/448 |
| 6,372,920 B1 | | 4/2002 | Minaskanian et al. | 549/75 |
| 6,393,318 B1 | | 5/2002 | Conn et al. | 604/20 |
| 6,398,562 B1 | | 6/2002 | Butler et al. | 439/91 |
| 6,465,004 B1 | | 10/2002 | Rossi-Montero | 424/448 |
| 6,514,530 B2 | | 2/2003 | Skluzacek | 424/464 |

(Continued)

FOREIGN PATENT DOCUMENTS

CA    2 532 804    2/2005

(Continued)

OTHER PUBLICATIONS

Goodman and Gilman's, The Pharmaclogical Basis of Therapeutics, 1990, Pergamon Press, 8th Edition, p. 160.*

(Continued)

*Primary Examiner* — Abigail Fisher

(74) *Attorney, Agent, or Firm* — Harness, Dickey & Pierce, P.L.C.

(57) ABSTRACT

An improved transdermal delivery system (TDS) comprises a self-adhesive matrix comprising a solid or semi-solid semi-permeable polymer which contains an amine-functional drug in its free base form as a multitude of microreservoirs within the matrix. The self-adhesive matrix is highly permeable to the free base of the amine-functional drug and is impermeable to the protonated form of the amine-functional drug.

17 Claims, 7 Drawing Sheets

U.S. PATENT DOCUMENTS

| | | | |
|---|---|---|---|
| 6,620,429 B1 | 9/2003 | Müller | |
| 6,685,959 B1 | 2/2004 | Moreau et al. | 424/449 |
| 6,884,434 B1 * | 4/2005 | Muller et al. | 424/487 |
| 6,899,894 B1 | 5/2005 | Klein | 424/448 |
| 6,929,901 B2 | 8/2005 | Liu | 430/329 |
| 7,279,178 B1 | 10/2007 | Berthold | 424/443 |
| 7,309,497 B2 | 12/2007 | Rimpler et al. | 424/422 |
| 7,413,747 B2 | 8/2008 | Mueller et al. | 424/448 |
| 2001/0053777 A1 | 12/2001 | Brecht | 514/221 |
| 2002/0004065 A1 | 1/2002 | Kanios | 424/449 |
| 2002/0110585 A1 | 8/2002 | Godbey et al. | 424/449 |
| 2003/0026830 A1 | 2/2003 | Lautertback et al. | 424/449 |
| 2003/0027793 A1 | 2/2003 | Lautertback et al. | 514/63 |
| 2003/0065086 A1 | 4/2003 | Kosal | 524/588 |
| 2003/0166709 A1 | 9/2003 | Rimpler et al. | 514/447 |
| 2004/0013620 A1 * | 1/2004 | Klose et al. | 424/59 |
| 2004/0034083 A1 | 2/2004 | Stephenson et al. | 514/406 |
| 2004/0048779 A1 | 3/2004 | Schollmayer | 514/2 |
| 2004/0057985 A1 | 3/2004 | Bracht | 424/449 |
| 2004/0110673 A1 | 6/2004 | Steinkasserer et al. | 514/12 |
| 2004/0116537 A1 | 6/2004 | Li et al. | 514/663 |
| 2004/0137045 A1 | 7/2004 | Breitenbach et al. | 424/449 |
| 2004/0202710 A1 * | 10/2004 | Muller | 424/449 |
| 2004/0209861 A1 | 10/2004 | Benavides et al. | 514/210.01 |
| 2005/0033065 A1 | 2/2005 | Mueller et al. | 549/74 |
| 2005/0079206 A1 * | 4/2005 | Schacht et al. | 424/449 |
| 2005/0136101 A1 | 6/2005 | Berthold | 424/448 |
| 2005/0175678 A1 | 8/2005 | Breitenbach | 424/448 |
| 2005/0175680 A1 | 8/2005 | Morgan et al. | 424/449 |
| 2005/0197385 A1 | 9/2005 | Scheller et al. | 514/438 |
| 2005/0260254 A1 | 11/2005 | Breitenbach et al. | 424/449 |
| 2006/0222691 A1 | 10/2006 | Cantor et al. | 424/448 |
| 2006/0263419 A1 | 11/2006 | Wolff | 424/448 |
| 2007/0072917 A1 | 3/2007 | Scheller et al. | 514/357 |
| 2007/0093546 A1 | 4/2007 | Scheller et al. | 514/447 |
| 2007/0191308 A1 | 8/2007 | Kramer | 514/60 |
| 2007/0191470 A1 | 8/2007 | Scheller | 514/438 |
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller et al. | 514/357 |
| 2008/0274061 A1 | 11/2008 | Schollmayer et al. | 424/45 |
| 2009/0143460 A1 | 6/2009 | Wolff et al. | 514/438 |

FOREIGN PATENT DOCUMENTS

| | | |
|---|---|---|
| CA | 2 532 859 | 2/2005 |
| CA | 2 547 820 | 6/2005 |
| CA | 2 546 797 | 7/2005 |
| DE | 198 14 083 | 10/1999 |
| DE | 19958554 A1 * | 1/2001 |
| DE | 19940238 | 3/2001 |
| DE | 100 60 550 | 4/2002 |
| EP | 1 256 340 | 11/2002 |
| FR | 2 792 529 | 10/2000 |
| WO | WO 93/07842 | 4/1993 |
| WO | WO 93/14727 | 8/1993 |
| WO | WO 93/16073 | 8/1993 |
| WO | WO 94/04109 | 3/1994 |
| WO | WO 94/07468 | 4/1994 |
| WO | WO 95/00122 | 1/1995 |
| WO | WO 95/01767 | 1/1995 |
| WO | WO 95/05137 | 2/1995 |
| WO | WO 95/05138 | 2/1995 |
| WO | WO 96/00110 | 1/1996 |
| WO | WO 96/22083 | 7/1996 |
| WO | WO 96/22084 | 7/1996 |
| WO | WO 96/40087 | 12/1996 |
| WO | WO 97/09971 | 3/1997 |
| WO | WO 97/29735 | 8/1997 |
| WO | WO 98/00126 | 1/1998 |
| WO | WO 99/49852 | 10/1999 |
| WO | WO 02/26217 | 4/2002 |
| WO | WO 02/45699 | 6/2002 |
| WO | WO 02/074286 | 9/2002 |
| WO | WO 2004/012719 | 2/2004 |
| WO | WO 2004/012730 | 2/2004 |
| WO | WO 2004/058247 | 7/2004 |

OTHER PUBLICATIONS

Nugroho et al., Pharmaceutical Research, 2004, 21(5), 844-850.*

Stryer, Biochemistry, 1996, W.H.Freeman and Company, New York, pp. 20-22 and 25.*

Roy, Samir D., et al., "Transdermal Delivery of Narcotic Analgesics: pH, Anatomical, and Subject Influences on Cutaneous Permeability of Fentanyl and Sufentanil". Pharmaceutical Research, vol. 7, No. 8, pp. 842-847, 1990.

Roy, Samir D., et al., "Controlled Transdermal Delivery of Fentanyl: Characterization of Pressure-Sensative Adhesives for Matrix Patch Design". Journal of Pharmaceutical Sciences, vol. 85, No. 5, pp. 491-495, May 1996.

Blindauer (2003) *Arch. Neurol.* 60(12): 1721-1728.

Chiang et al. (1995) *Proceed Intern. Symp. Control Rel. Bioact Mater* 22, 710-711.

Hammond (1989) Handbook of Pressure Sensitive Adhesive Technology $2^{nd}$ Ed. Chapter 4, p. 38.

Hsu and Roos (1992) *Cygnus Therapeutic Systems Project Report N-0923*, 2-19.

Levien (2005) *Advances in Pharmacy* 3(1), 62-92.

LeWitt (2007) *Neurology* 68, 1262-1267.

Loschmann et al. (1989) *Eur. J. Pharmacol.* 166, 373-380.

Miyamoto et al. (1994) *Analyst* 119, 1489.1492.

Pfister (1988) *Drug and Chem. Ind.* (Oct): 44-52.

Pfister (1989) *Pharm. Tech.* (March): 126-138.

Pfister and Hsieh (1990) *Pharm. Tech.* (Sept): 132-140.

Pfister and Hsieh (1990) *Pharm. Tech.* (Oct): 54-60.

Pfister et al. (1991) *Chemistry in Britain* (Jan): 43-46.

Pfister et al. (1992) *Pharm. Tech.* (Jan): 42-58 and 83.

Pharmacopeia (2002) USP25/NF20, Chapter 724.

Tanojo et al. (1997) *J. Controlled Release* 45, 41-47.

Thomas (1991) *STP Pharma Science* 1(1): 38-46.

Tozer (1995) *Clinical Pharmakinetics Concepts and Applications* $3^{rd}$ ed. pp. 480-483.

Ulman et al. (1998) Information Brochure, Dow Corning Corp., USA.

The Merck Index, Thirteenth Edition (2001) "7024. Oxybutynin" Whitehouse Station, NJ: Merck & Co., Inc., p. 1245.

Van der Weide, et al. (1988) "The enantiomers of the D-2 dopamine receptor agonist N-0437 discriminate between pre- and postsynaptic dopamine receptors." Eur J Pharmacol 146:319-326.

Office Action, dated Aug. 17, 2007 issued in U.S. Appl. No. 10/623,864.

Office Action, dated Nov. 12, 2008 issued in U.S. Appl. No. 10/623,864.

Office Action, dated Jun. 24, 2009 issued in U.S. Appl. No. 10/623,864.

Office Action, dated Jan. 6, 2010 issued in U.S. Appl. No. 10/623,864.

Neupro (2007) Rotigotine Transdermal System.

Neupro (2008) Request to initiate Neupro.

Office Action, dated Jun. 9, 2010 issued in U.S. Appl. No. 11/931,762.

Office Action, dated Apr. 15, 2002 issued in U.S. Appl. No. 09/647,290.

Office Action, dated Nov. 1, 2002 issued in U.S. Appl. No. 09/647,290.

Office Action, dated Aug. 31, 2010 issued in U.S. Appl. No. 10/623,864.

Office Action, dated Sep. 21, 2006 issued in U.S. Appl. No. 10/429,283.

Office Action, dated Jan. 8, 2008 issued in U.S. Appl. No. 10/429,283.

Office Action, dated Sep. 12, 2008 issued in U.S. Appl. No. 10/429,283.

Office Action, dated Mar. 30, 2009 issued in U.S. Appl. No. 10/429,283.

Office Action, dated Dec. 23, 2009 issued in U.S. Appl. No. 10/429,283.

Office Action, dated Oct. 1, 2010 issued in U.S. Appl. No. 10/429,283.

Office Action, dated Mar. 23, 2007 issued in U.S. Appl. No. 10/713,424.
Office Action, dated Sep. 14, 2007 issued in U.S. Appl. No. 10/713,424.
Office Action, dated Jun. 25, 2008 issued in U.S. Appl. No. 10/713,424.
Office Action, dated Feb. 19, 2009 issued in U.S. Appl. No. 10/713,424.
Office Action, dated Sep. 13, 2007 issued in U.S. Appl. No. 10/936,620.
Office Action, dated May 1, 2008 issued in U.S. Appl. No. 10/936,620.
Office Action, dated Jan. 26, 2009 issued in U.S. Appl. No. 10/936,620.
Office Action, dated Nov. 6, 2009 issued in U.S. Appl. No. 10/936,620.
Office Action, dated Oct. 8, 2010 issued in U.S. Appl. No. 10/936,620.
Office Action, dated Jan. 23, 2008 issued in U.S. Appl. No. 11/931,666.
Office Action, dated Mar. 6, 2009 issued in U.S. Appl. No. 10/517,157.
Office Action, dated Aug. 3, 2010 issued in U.S. Appl. No. 10/517,157.
Office Action, dated Oct. 15, 2009 issued in U.S. Appl. No. 10/139,894.

* cited by examiner

TRANSDERMAL DELIVERY SYSTEM

This application claims benefit of U.S. Provisional Patent Application No. 60/451,715 filed Mar. 5, 2003, the entire contents of which are hereby incorporated by reference in their entirety.

This application contains subject matter that is related to U.S. patent application Ser. No. 10/623,864 filed on Jul. 22, 2003.

FIELD OF INVENTION

The present invention relates to an improved transdermal delivery system for amine functional drugs. Moreover, the invention relates to a method of treatment using the transdermal delivery system.

TECHNICAL BACKGROUND

To date, various transdermal delivery systems (TDS) for the administration of amine functional drugs, such as rotigotine and many others, have been described. WO 94/07468 discloses a TDS containing rotigotine hydrochloride as active substance in a two-phase matrix, which is essentially formed by a hydrophobic polymer material as the continuous phase and a disperse hydrophilic phase contained therein and mainly containing the drug and hydrated silica. The silica is said to enhance the maximum possible loading of the TDS with the hydrophilic salt. Moreover, the formulation of WO 94/07468 usually contains additional hydrophobic solvents, permeation promoting substances, dispersing agents and, in particular, an emulsifier which is required to emulsify the aqueous solution of the active component in the lipophilic polymer phase. A TDS prepared by using such a system has been tested in healthy subjects and Parkinson's patients. However, no satisfactory drug plasma levels were achieved.

Various further TDSs have been described in WO 99/49852.

In the TDS according to WO 94/07468 and many related applications, passive diffusion membranes were used.

However, as the skin is to be seen as a very efficient barrier for most drug candidates, such type of membrane controlled systems are more or less limited in practice to transdermal delivery of active substances that reveal a very high skin permeability. Additionally, special requirements on drug release kinetics have to be met like contact delivery over several days.

An object of the present invention is to control (i.e. to canalise/manoeuvre) the transport of a drug substance towards and across the skin from a drug reservoir, thereby enhancing the flux of the drug substance across the TDS/skin interface.

A further object and aspect of the present invention is to provide a suitable composition and manufacturing methods of polymer matrices in TDS which lead to an enhanced delivery of weakly basic amines to and across the skin by
(i) preventing back diffusion of the drug portion which is ionized in the skin according to its pKa value from the skin tissue into the TDS,
(ii) offering continuous delivery of the active compound across the stratum corneum not only via the common more lipophilic route (e.g. intercellular) but also through hydrophilic pores (e.g. eccrine sweat glands).

SUMMARY OF THE INVENTION

There is now provided a TDS comprising a backing layer inert to the components of the matrix, a self-adhesive matrix containing an amine functional drug, and a protective foil or sheet to be removed prior to use,
characterized in that
the self-adhesive matrix comprises a solid or semi-solid semi-adhesive polymer
(1) wherein an amine functional drug in its free base form is incorporated,
(2) which comprises a multitude of microreservoirs within the matrix, said microreservoirs containing the amine functional drug and optionally a crystallization inhibitor,
(3) which is permeable to the free base of the amine functional drug,
(4) which is substantially impermeable to the protonated form of the amine functional drug,
(5) wherein the maximum diameter of the microreservoirs is less than the thickness of the matrix.

DESCRIPTION OF THE INVENTION

The present invention provides a TDS for amine functional drugs providing a high steady state flux rate of the amine functional drug over the TDS/skin interface.

Surprisingly, it was found that drug release properties of a TDS having a silicone-type adhesive matrix containing an amine functional drug can be significantly enhanced by
(1) minimizing the amount of the amine functional drug which is present in the protonated form (salt form);
(2) incorporating the amine functional drug in a multitude of microreservoirs within the self-adhesive matrix consisting of a solid or semi-solid semi-permeable polymer.

Figure 1:
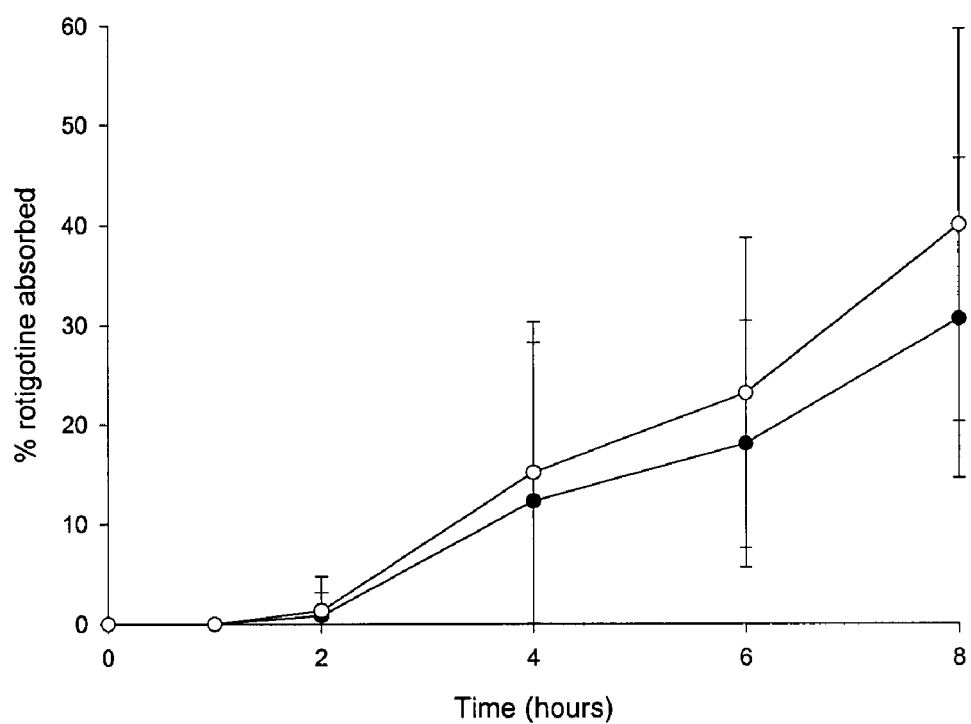
FIG. 1 shows the effect of the protonation of the drug in the semi-permeable matrix on the drug absorption.
Figure 2:
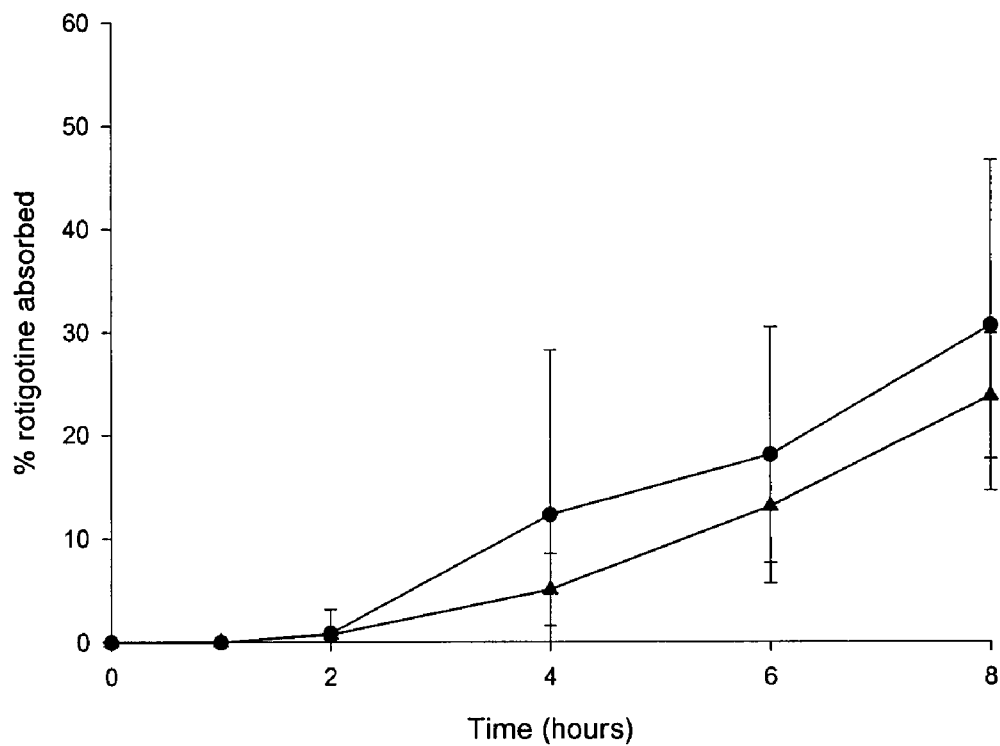
FIG. 2 shows the impact of the size distribution of the microreservoirs in the semi-permeable matrix on the drug absorption.
Figure 3:
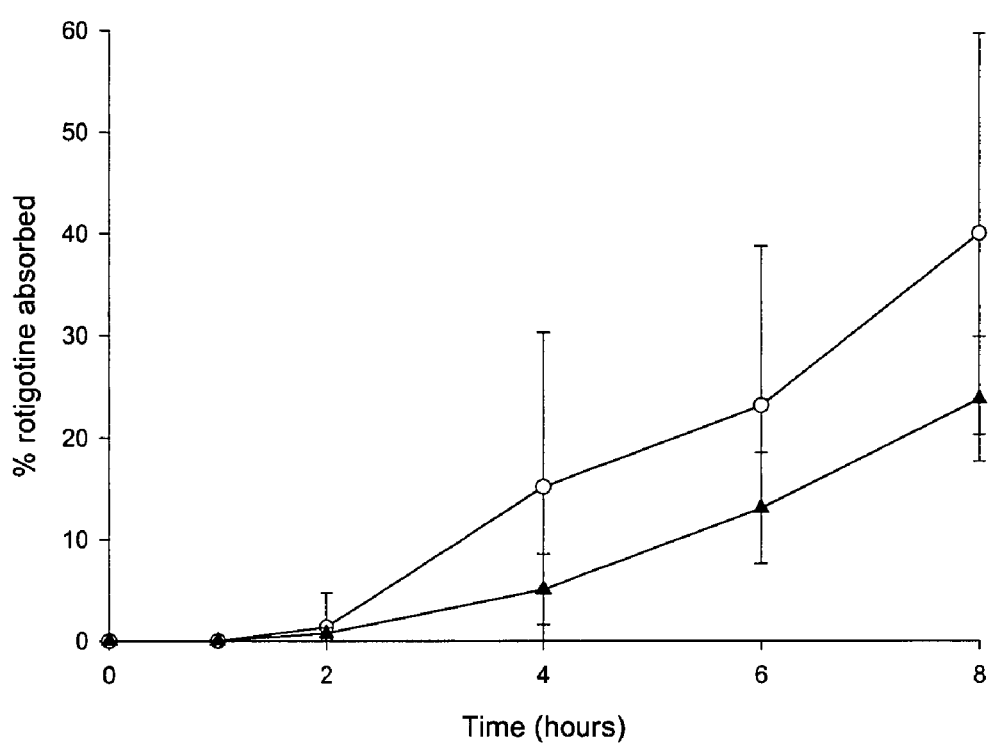
FIG. 3 shows the effect of reducing the amount of the protonated form of the drug in the semi-permeable matrix and reducing the size of the microreservoirs on the drug absorption.

The impact of above described measures on drug release characteristics of rotigotine in vivo is illustrated in FIGS. 1, 2 and 3. The relative drug absorption in vivo was highest for the sample according to the invention; increase of the size of the microreservoirs and/or the amount of drug salt residues in the TDS led to slower initial drug release.

Based on the above findings, the present invention was accomplished.

When using the TDS, according to the present invention, a high transfer of the amine functional drug from the silicone matrix into the outermost skin layer can be achieved. Consequently, plasma values of the amine functional drug are sufficient to allow for a reasonable expectation that an efficient treatment with these drugs with fewer side effects can be provided.

It should be understood that the term "treatment" in the context of this application is meant to designate a treatment or an alleviation of the symptoms of the diseases that can be treated with the amine functional drugs useful in this invention. The treatment may be of a therapeutic or prophylactic nature.

In a preferred embodiment the amine functional drug incorporated in the TDS of the present invention has an octanol/water partitioning coefficient log P>_2.8 at pH 7.4. In another preferred embodiment the amine functional drug has a pKa of 7.4 to 8.4. In an especially preferred embodiment the amine functional drug has an octanol/water partitioning coefficient log P>_2.8 at pH 7.4 and a pKa of 7.4 to 8.4. The pKa-value can be measured by standard methods. A particularly preferred method is potentiometric titration of aqueous solutions (without addition of organic cosolvents) at room temperature. The octanol/water partitioning coefficients (octan-l-of/water partitioning coefficients) are determined at pH 7.4, 37° C. and an ionic strength of 0.15 in an appropriate buffer solution according to the method described by E. Miyamoto et al. (E. Miyamoto et al. "Physico-chemical Properties of Oxybutynin" Analyst (1994), 119, 1489-1492).

Particularly preferred amine functional drugs are dopamine D2 agonists, which are useful for example in the treatment of Parkinson's disease. Especially preferred dopamine D2 receptor agonists are aminotetraline compounds, such as 5,6,7,8-tetrahydro-6-[propyl-[2-(2-thienyl)ethyl]amino]-1-naphthalenol (INN: rotigotine).

Other examples for particularly preferred amine functional drugs are N-phenyl-N-[1-(2-phenylethyl)-4-piperidinyl]propanamide (INN: fentanyl) which is useful in the treatment of pain and anticholinergic drugs exerting an antispasmodic effect on smooth muscles and inhibiting the muscarinic action of acetylcholin on smooth muscles. Examples of such anticholinergic drugs which are useful in the present invention are 4-diethylamino-2-butynyl phenylcyclohexyl-glycolate (INN: oxybutynine) and 2-[3-(diisopropylamino)-1-phenylpropyl]-4-(hydroxymethyl)phenyl isobutyrate (INN: fesoterodine). Oxybutynine and fesoterodine are useful in the treatment of urinary incontinence.

It will be understood by a person skilled in the art that the amine functional drugs, such as rotigotine, fentanyl, oxybutynine and fesoterodine, may all exist in various isomeric forms. It has to be understood that in this case the amine functional drug may be any single isomer or a mixture of different isomers. If the amine functional group contains asymmetric carbon atoms, any single enantiomer or a mixture of enantiomers may be used. Rotigotine, fentanyl oxybutynine and fesoterodine all contain one asymmetric carbon atom. Hence, the S- or R-enantiomer or the racemate or any other enantiomer mixture of these compounds may be used as the amine functional drug.

At least a part of the amine functional drug is contained in a multitude of microreservoirs distributed within the self-adhesive matrix of the TDS according to the invention. This does not exclude and will normally even imply that a certain fraction of the amine functional drug is dissolved in the solid or semi-solid semi-permeable polymer of the matrix at its saturation concentration.

Within this specification "microreservoirs" are meant to be understood as particulate, spatially and functionally separate compartments consisting of pure drug or a mixture of drug and crystallization inhibitor, which are dispersed in the self-adhesive (polymer) matrix. Preferably the self-adhesive matrix contains $10^3$ to $10^9$ microreservoirs per $cm^2$ of its surface, particularly preferred are $10^6$ to $10^9$ microreservoirs per $cm^2$.

The amine functional drug is incorporated in the self-adhesive matrix in its free base form. This does not totally exclude the presence of some residual salt form of the amine functional drug in the final TDS. However, the salt form of the amine functional drug should be contained in the self-adhesive matrix of the final TDS in an amount of preferably less than 5%, more preferably less than 2%, particularly less than 1% (w/w).

If the amine functional drug is present in the self-adhesive matrix in its protonated (salt) form, it will not be released by the self-adhesive matrix. Thus, the amount of the salt form of the amine functional drug can be determined by performing a drug dissolution test according to the Paddle over Disk method as described in the United States Pharmacopeia (United States Pharmacopeia/New Formulary (USP25/NF20), Chapter 724 "Drug Release", United States Pharmacopeial Convention, Inc., Rockville, Md. 20852, U.S.A. (2002)), using the following conditions: dissolution medium: 900 ml phosphate buffer pH 4.5; temperature adjusted to 32±0.5° C.; paddle rotation speed: 50 rpm; sampling times: 0.5, 1, 2 and 3 h, respectively. The increase in the eluted drug concentration can be used to calculate the amount of unprotonated drug in the matrix.

The amount of the salt form of the amine functional drug may be reduced e.g. by reducing the water content of the mass containing the drug and organic solvent(s). In a particularly preferred embodiment of the invention the water content is reduced during manufacture to preferably less than 0.4% (w/w), more preferably less than 0.1%, of the mass.

A further step, which may be taken for reducing the amount of the salt form of the amine functional drug, is isolating the free base form of the amine functional drug in solid form prior to the preparation of the TDS. If the free base of the amine functional drug is produced in situ during the manufacture of the TDS by neutralizing an acid addition salt, a certain residue of the ionized drug form will remain in the polymer matrix (usually >5% (w/w) and up to approximately 10%). Therefore, such in situ preparation of the free base form will generally not be suitable for practising the present invention.

The maximum diameter of the microreservoirs is less than the thickness of the matrix, preferably up to 70% of the thickness of the matrix, particularly preferably 5 to 60% of the thickness of the matrix. For an exemplary thickness of the matrix of 50 μm this corresponds to a maximum diameter of the microreservoirs in the range of preferably up to 35 μm. The term "maximum diameter" is meant to be understood as the diameter of the microreservoirs in one dimension (x-, y-, or z-dimension), which is the largest. It is clear to the skilled person that in case of spherical diameters the maximum diameter corresponds to the microreservoir's diameter. However, in the case of microreservoirs, which are not shaped in the form of spheres—i.e. of different geometric forms—, the x-, y- and z-dimensions may vary greatly.

As the maximum diameter of the microreservoirs in the direction of the cross-section of the matrix, i.e. between the release surface and the backing layer, is less than the thickness of the matrix, direct contact between the skin and the basic microreservoirs containing the amine-functional drug is avoided, if not at all prevented. Owing to the slightly acidic pH of the skin, direct contact between the skin and the microreservoirs in the matrix leads to protonation of the amine-functional drug, thereby deteriorating the semi-permeability of the matrix.

In a particularly preferred embodiment of the invention, the mean diameter of the microreservoirs containing the amine functional drugs distributed in the matrix is in the range of 1 to 40%, even more preferably 1 to 20%, of the thickness of the drug-loaded self-adhesive matrix. For an exemplary thickness of the matrix of 50 µm this corresponds to a mean diameter of the microreservoirs in the range of preferably 0.5 to 20 µm. The term "mean diameter" is defined as the mean value of the x,y,z-average diameters of all microreservoirs. The target particle size can be adjusted by the solids content and viscosity of the drug-containing coating mass.

The maximum and mean diameters of the microreservoirs as well as the number of microreservoirs per surface area of the self-adhesive matrix can be determined as follows: The release liner is removed from the TDS, and the free adhesive surface is examined with a light microscope (Leica microscope type DM/RBE equipped with a camera type Basler A 113C). The measurement is performed by incidental polarized light analysis using a microscope at 200× magnification. A picture analysis is performed using the software Nikon Lucia_Di, Version 4.21, resulting in mean and maximum diameters for each sample.

The TDS of the present invention is of the "matrix" type. In such matrix type TDS the drug is dispersed in a polymer layer. The TDS of the matrix type in their simplest version comprise a one-phase (monolayer) matrix. They consist of a backing layer, a self-adhesive matrix containing the active agent and a protective foil or sheet, which is removed before use.

Versions that are more complicated comprise multi-layer matrixes, wherein the drug may be contained in one or more non-adhesive polymer layers. The TDS of the present invention is preferably a one-phase (mono layer) matrix system.

The solid or semi-solid semi-permeable polymer of the self-adhesive matrix has to satisfy the following requirements:
1. Sufficient solubility and permeability for the free base form of the amine functional drug.
2. Impermeability for the protonated form of the amine functional drug.

In a particular preferred embodiment of the invention the self-adhesive matrix is free of particles that can absorb salts of the amine functional drug on the TDS/skin interface. Examples of particles that can absorb salts of the amine functional drug on the TDS/Skin interface include silica. Such particles that can adsorb salts of the amine functional drug may represent diffusion barriers for the free base form of the drug and may result in the formation of channels inducing some permeability of the self-adhesive matrix for the protonated form of the drug. Such embodiments are therefore disadvantageous for practising the invention.

The self-adhesive matrix of the TDS of the present invention comprises a solid or semi-solid semi-permeable polymer. Usually this polymer will be a pressure sensitive adhesive (PSA) or a mixture of such adhesives. The pressure sensitive adhesive(s) form a matrix in which the active ingredient and the other components of the TDS are incorporated.

The adhesive used in the present invention should preferably be pharmaceutically acceptable in a sense that it is biocompatible, non-sensitising and non-irritating to the skin. Particularly advantageous adhesives for use in the present invention should further meet the following requirements:
1. Retained adhesive and co-adhesive properties in the presence of moisture or perspiration, under normal temperature variations,
2. Good compatibility with the amine functional drug, as well as with the further excipients used in the formulation.

Although different types of pressure sensitive adhesive may be used in the present invention, it is preferred to use lipophilic adhesives having both a low drug and low water absorption capacity. Particular preferably, the adhesives have solubility parameters which are lower than those of the amine functional drugs. Such preferred pressure sensitive adhesives for use in the TDS of the present invention are silicone type pressure sensitive adhesives. Especially preferred pressure sensitive adhesives for use in the TDS of the invention are of the type forming a soluble polycondensed polydimethylsiloxane (PDMS)/resin network, wherein the hydroxy groups are capped with e.g. trimethylsilyl (TMS) groups. Preferred adhesives of this kind are the BIO-PSA silicone pressure sensitive adhesives manufactured by Dow Corning, particularly the Q7-4201 and Q7-4301 qualities. However, other silicone adhesives may also be used.

In a further and especially preferred aspect, two or more silicone adhesives are used as the main adhesive components. It can be advantageous if such a mixture of silicone adhesives comprises a blend of high tack silicone pressure sensitive adhesive comprising polysiloxane with a resin and a medium tack silicone type pressure sensitive adhesive comprising polysiloxane with a resin.

Tack has been defined as the property that enables an adhesive to form a bond with the surface of another material upon brief contact under light pressure (see e.g. "Pressure Sensitive Tack of Adhesives Using an Inverted Probe Machine", ASTM D2979-71 (1982); H. F. Hammond in D. Satas "Handbook of Pressure Sensitive Adhesive Technology" (1989), $2^{nd}$ ed., Chapter 4, Van Nostrand Reinhold, New York, page 38).

Medium tack of a silicon pressure sensitive adhesive indicates that the immediate bond to the surface of another material is weaker compared to high tack silicon adhesive. The mean resin/polymer ratio is approx. 60/40 for medium tack adhesives, whereas it is approx. 55/45 for high tack adhesives. It is known to the skilled person that both tape and Theological properties are significantly influenced by the resin/polymer ratio (K. L. Ulman and R. P. Sweet "The Correlation of Tape Properties and Rheology" (1998), Information Brochure, Dow Corning Corp., USA).

Such a blend comprising a high and a medium tack silicone type pressure sensitive adhesive comprising polysiloxane with a resin is advantageous in that it provides for the optimum balance between good adhesion and little cold flux. Excessive cold flux may result in a too soft patch which easily adheres to the package or to patient's garments. Moreover, such a mixture seems to be particularly useful for obtaining higher plasma levels. A mixture of the aforementioned Q7-4201 (medium tack) and Q7-4301 (high tack) proved to be especially useful as a matrix for the TDS according to the present invention.

In a further preferred embodiment, the TDS further includes a crystallization inhibitor. Several surfactants or amphiphilic substances may be used as crystallization inhibitors. They should be pharmaceutically acceptable and approved for use in medicaments. A particularly preferred example of such a crystallization inhibitor is soluble polyvinylpyrrolidone, which is commercially available, e.g. under the trademark Kollidon® (Bayer AG). Other suitable crystallization inhibitors include copolymers of polyvinylpyrrolidone and vinyl acetate, polyethyleneglycol, polypropyleneglycol, glycerol and fatty acid esters of glycerol or copolymers of ethylene and vinyl acetate.

The device of the present invention further comprises a backing layer, which is inert to the components of the matrix. This backing layer is a film being impermeable to the active compounds. Such a film may consist of polyester, polyamide, polyethylene, polypropylene, polyurethane, polyvinyl chloride or a combination of the aforementioned materials. These films may or may not be coated with an aluminium film or with aluminium vapour. The thickness of the backing layer may be between 10 and 100 μm, preferably between 15 and 40 μm.

The TDS of the present invention further comprises a protective foil or sheet, which will be removed immediately prior to use, i.e. immediately before the TDS will be brought into contact with the skin. The protective foil or sheet may consist of polyester, polyethylene or polypropylene which may or may not be coated with aluminium film or aluminium vapour or fluoropolymers. Typically the thickness of such a protective foil or sheet ranges from between 50 and 150 μm. So as to facilitate removal of the protective foil or sheet when wishing to apply the TDS, the protective foil or sheet may comprise separate protective foils or sheets having overlapping edges, similar to the kind used with the majority of conventional plasters.

In a preferred embodiment of the present invention, the TDS has a basal surface area of 5 to 50 cm$^2$, particularly of 10 to 30 cm$^2$. It goes without saying that a device having a surface area of, say, 20 cm$^2$ is pharmacologically equivalent to and may be exchanged by two 10 cm$^2$ devices or four 5 cm$^2$ devices having the same drug content per cm$^2$. Thus, the surface areas as indicated herein should be understood to refer to the total surface of all devices simultaneously administered to a patient.

Providing and applying one or several TDS according to the invention has the pharmacological advantage over oral therapy that the attending physician can titrate the optimum dose for the individual patient relatively quickly and accurately, e.g. by simply increasing the number or size of devices given to the patient. Thus, the optimum individual dosage can often be determined after a time period of only about 3 weeks with low side effects.

A preferred content of the amine functional drug in the TDS according to the invention is in the range of 0.1 to 2.0 mg/cm$^2$. Still more preferred are 0.20 to 1.0 mg/cm$^2$. If a 7 day patch is desired, higher drug contents will generally be required.

The device used in the present invention is preferably a patch having a continuous adhesive matrix in at least its center portion containing the drug. However, transdermal equivalents to such patches are likewise comprised by the present invention, e.g. an embodiment where the drug is in an inert but non-adhesive matrix in the center portion of the device and is surrounded by an adhesive portion along the edges.

The TDS according to the present invention is prepared by a manufacturing process, which comprises preparing a drug loaded adhesive, coating, drying or cooling and lamination to get the bulk product, converting the laminate into patch units via cutting, and packaging.

The invention and the best mode for carrying it out will be explained in more detail in the following non-limiting examples.

Invention Example 1

Very Low Salt Content, Small Microreservoirs 252.6 g Rotigotine free base are dissolved in 587.8 g ethanol 100% w/w and mixed with 222.2 g ethanolic solution containing 25% w/w polyvinylpyrrolidone (Kollidon F 90), 0.11% w/w aqueous sodium bisulfite solution (10% w/w), 0.25% ascorbyl palmitate and 0.62% DL-α-tocopherol. To the homogenous mixture 1692.8 g BIO-PSA Q7 4301 (73% w/w), 1691.6 g BIO-PSA Q7 4201 (73% w/w) and 416.3 g petrol ether are added and all components are stirred for at least 1 hour to get a homogenous dispersion.

For manufacture of the patch matrix, the dispersion is coated onto a suitable release liner (for example Scotchpak 1022) and the solvents are continuously removed in a drying oven at temperatures up to 80° C. to get a drug-containing adhesive matrix of 50 g/m$^2$ coating weight. The dried matrix film is laminated with a polyester-type backing foil which is siliconized on the inner side and aluminium vapor coated on the opposite side.

The individual patches are punched out of the complete laminate and are sealed into pouches under a nitrogen flow. The rotigotine contained in the matrix was quantitatively released after 3 hours in the drug dissolution test according to the Paddle over Disk method as described in the USP using the conditions as described above. This result indicates that the obtained TDS was completely free of rotigotine hydrochloride.

Figure 5:
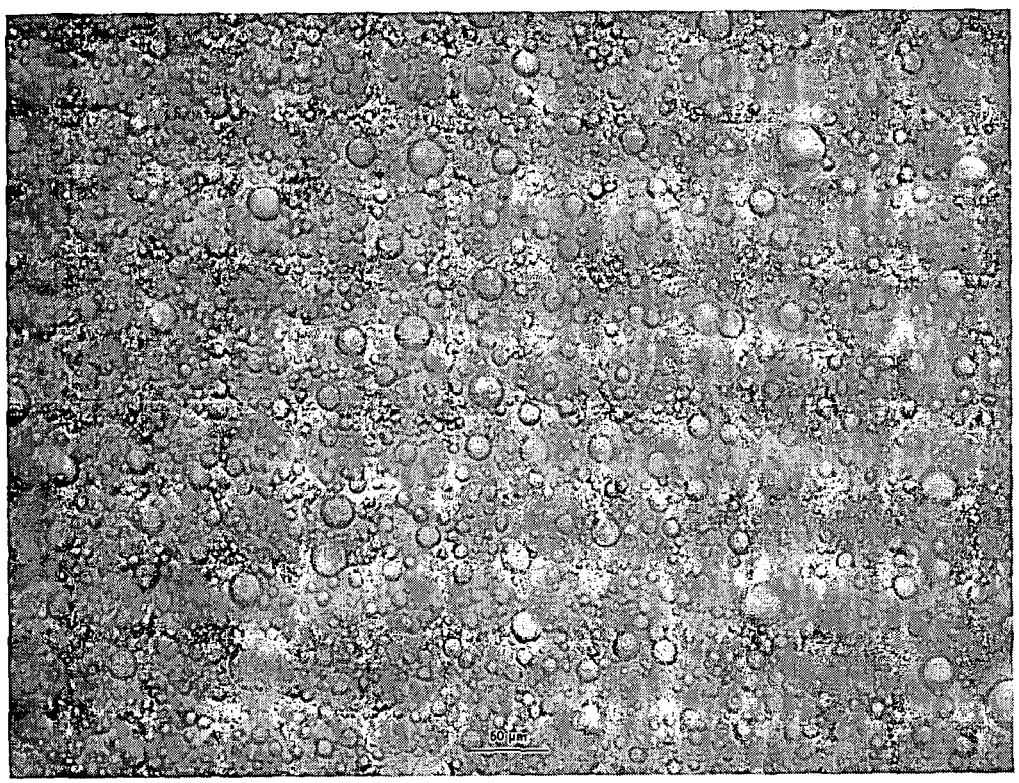
FIG. 5 shows a microscope image of the TDS according to the invention.

The mean size of the microreservoirs in the TDS was approx. 10 μm with typical sizes in the range of 5 to 35 μm. A microscope image of the obtained TDS is shown in FIG. 5.

Comparative Example 1

High Salt Content, Small Microreservoirs 2400 g Rotigotine hydrochloride were added to a solution of 272.8 g NaOH in 3488 g ethanol (96%). The resulting mixture was stirred for approximately 10 minutes. Then 379.2 g of sodium phosphate buffer solution (27.6 g Na$_2$HPO$_4$×2H$_2$O) and 53.2 g Na$_2$HPO$_4$×2H$_2$O in 298.5 g water) was added. Insoluble or precipitated solids were separated from the mixture by filtration. The filter was rinsed with 964 g ethanol (96%) to obtain a particle-free ethanolic solution of rotigotine essentially in the form of the free base.

The rotigotine solution (6150 g) in ethanol (30% w/w) was mixed with 407 g ethanol (96%). The resulting solution was mixed with 1738.8 g of an ethanolic solution containing 25 wt. % polyvinylpyrrolidone (Kollidone® 90F), 0.11 wt. % aqueous sodium bisulfite solution (10 wt. %), 0.25 wt. % ascorbyl palmitate, and 0.62 wt. % DL-alpha-tocopherol until homogeneity. To the mixture 13240 g of an amine resistant high tack silicone adhesive (BIO-PSA® Q7-4301 mfd. by Dow Corning) (73 wt. % solution in heptane), 13420 g of an amine resistant medium tack silicone adhesive (BIO-PSA® Q7-4201 mfd. by Dow Corning) (72 wt. % solution in heptane), and 3073 g petrol ether were added, and all components were stirred until a homogenous dispersion was obtained.

The dispersion was coated onto a suitable polyester release liner (SCOTCHPAK® 1022) with a suitable doctor knife and the solvents were continuously removed in a drying oven at temperatures up to 80° C. for about 30 minutes to obtain a drug containing adhesive matrix of 50 g/m$^2$ coating weight. The dried matrix film was laminated with a polyester-type backing foil (SCOTCHPAK® 1109). The individual patches were punched out of the complete laminate in the desired sizes (e.g. 10 cm$^2$, 20 cm$^2$, 30 cm$^2$) and sealed into pouches under the flow of nitrogen.

Only approx. 95% of the rotigotine contained in the matrix were released after 3 hours in the drug dissolution test according to the Paddle over Disk method as described in the USP using the conditions as described above. Thus, the obtained TDS contained approx. 5% (w/w) of protonated rotigotine.

The mean size of the microreservoirs in the TDS was approx. 15 μm with typical sizes in the range of 10 to 20 μm.

Comparative Example 2

High Salt Content, Large Microreservoirs 150 g Rotigotine hydrochloride were added to a solution of 17.05 g NaOH in 218 g ethanol (96%). The resulting mixture was stirred for approximately 10 minutes. Then 23.7 g of sodium phosphate buffer solution (8.35 g $Na_2HPO_4 \times 2H_2O$ and 16.07 g $NaH_2PO_4 \times 2H_2O$ in 90.3 g water) was added. Insoluble or precipitated solids were separated from the mixture by filtration. The filter was rinsed with 60.4 g ethanol (96%) to obtain a particle-free ethanolic solution of rotigotine essentially in the form of the free base.

The rotigotine solution (346.4 g) in ethanol (35% w/w) was mixed with 36.2 g ethanol (96%). The resulting solution was mixed with 109 g of an ethanolic solution containing 25 wt % polyvinylpyrrolidone (KOLLIDON® 90F), 0.077 wt % aqueous sodium bisulfite solution (10 wt %), 0.25 wt % ascorbyl palmitate, and 0.63 wt % DL-alpha-tocopherol until homogenous. To the mixture, 817.2 g of an amine resistant high tack silicone adhesive (BIO-PSA® Q7-4301 mfd. by Dow Corning) (74 wt % solution in heptane), 851.8 g of an amine resistant medium tack silicone adhesive (BIO-PSA® Q7-4201 mfd. by Dow Corning) (71 wt % solution in heptane), and 205.8 g petrol ether (heptane) were added, and all components were stirred until a homogenous dispersion was obtained.

The dispersion was coated onto a suitable polyester release liner (SCOTCHPAK® 1022) with a suitable doctor knife and the solvents were continuously removed in a drying oven at temperatures up to 80° C. for about 30 min to obtain a drug-containing adhesive matrix of 50 g/m² coating weight. The dried matrix film was laminated with a polyester-type backing foil (SCOTCHPAK® 1109). The individual patches were punched out of the complete laminate in the desired sizes (e.g. 10 cm², 20 cm², 30 cm²) and sealed into pouches under the flow of nitrogen.

Owing to the large microreservoirs in the TDS' matrix, it was possible to dissolve the rotigotine salts by direct contact with the dissolution medium. Thus, it was not possible to determine the amount of the protonated form of rotigotine. This indicates that the maximum diameter of the microreservoirs was larger than the thickness of the matrix.

Figure 4:
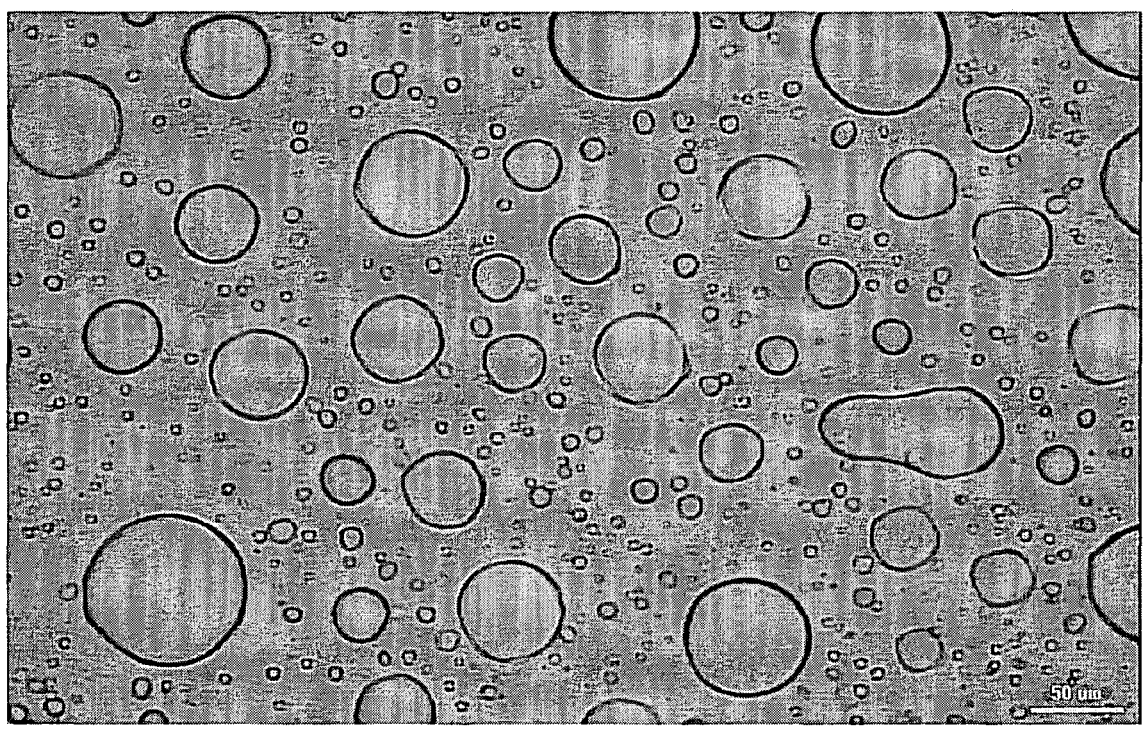
FIG. 4 shows a microscope image of a conventional TDS.

The mean size of the microreservoirs in the TDS was approx. 50 μm with typical sizes in the range of 20 to 90 μm. A microscope image of the obtained TDS is shown in FIG. 4.

As rotigotine was released from rotigotine hydrochloride in a manner similar to Comparative Example 1, one may conclude that the obtained TDS also contained 5% (w/w) of rotigotine in its protonated form.

Comparative Example 3

Acrylate-Type Formulation

A mixture of 50.0 g rotigotine hydrochloride and 28.6 g sodium trisilicate in 95 g methyl ethyl ketone was stirred at room temperature for 48 hours. Subsequently, 17.9 g oleic alcohol, 128.6 g of an acrylic-type adhesive solution (51.4% w/w in ethyl acetate; trade name: Durotak® 387-2287 from NATIONAL STARCH & CHEMICAL), 33.0 g of EUDRAGIT® E100 (from ROEHM PHARMA) (50% w/w solution in ethyl acetate) and 45.0 g ethyl acetate were added, and the mass was homogenised mechanically.

The dispersion was coated onto a suitably siliconised process liner (Hostaphan® RN 100), and the solvents were evaporated at 50° C. over 30 minutes, thereby obtaining a matrix weight of 60 g/m². The dry film was laminated with a suitable polyester foil (Hostaphan® RN 15). Individual patches having a desired size of (e.g. 20 cm²) were punched out of the resulting laminate and sealed into pouches under the flow of nitrogen.

Example 2

In Vivo Drug Absorption Test

In order to monitor the absorption of the amine functional drug by the human skin the following experiment was carried out. The test was performed with the TDS obtained in Example 1 as well as in Comparative Examples 1 and 2.

The plasma concentration time profile at different test times was determined in pharmacokinetic studies involving (A) 14 healthy male persons (TDS of Comparative Examples 2 and 3) or (B) 30 healthy male persons (TDS of Example 1 and Comparative Example 1), respectively. The studies were conducted following an open single-dose randomised (B) two-way or (A) three-way cross-over design.

Individual concentrations of rotigotine were determined by means of liquid chromatography and mass spectroscopy. The lower limit of quantification (LOQ) was 10 pg/ml.

The drug absorption was calculated from the plasma concentration data according to the Wagner-Nelson method (Malcom Rowland, Thomas N. Tozer (Eds.) "Estimation of Adsorption Kinetics from Plasma Concentration Data" in Clinical Pharmacokinetics, pp 480-483, Williams & Wilkins, 1995), 100%=absorption rate after 48 hours; patch application time was 24 hours.

A comparison of the flux across human skin for the different TDS tested is shown in FIGS. 1, 2 and 3.

In FIG. 1 the rotigotine absorption for the sample obtained in Example 1 containing no salt (○) is compared to the sample obtained in Comparative Example 1 containing approx. 5% (w/w) of rotigotine hydrochloride (●). The comparison in FIG. 1 clearly shows that the drug absorption after patch application depends on the residual salt content in the semi-permeable matrix and is significantly improved by reducing the amount of the protonated form of the amine-functional drug present in the matrix.

FIG. 2 shows the impact of the size distribution of the microreservoirs distributed in the semi-permeable matrix by comparing the sample obtained in Comparative Example 1 having a mean microreservoir size of approx. 15 μm and typical sizes between 10 and 20 μm (●) with the sample obtained in Comparative Example 2 having a mean microreservoir size of approx. 50 μm and typical sizes between 20 and 90 μm (▲). From this comparison it can be deduced that reducing the size of the matrix reservoirs significantly increases the flux across the human skin.

A comparison between the TDS of Example 1 (○) and Comparative Example 2 (▲) is shown in FIG. 3. This comparison clearly indicates that the flux across human skin is significantly enhanced by reducing the salt content and decreasing the size of the microreservoirs.

Example 3

In Vitro Diffusion Experiment with Transdermal Drug Delivery Systems

The test was performed with a sandwich of consecutively a supportive separator membrane, skin and the TDS. Active substance that has diffused from the TDS through the skin and/or membrane dissolves in an acceptor liquid that continuously passes directly underneath the membrane; the acceptor liquid was collected in tubes in a fraction collector; and the fractions were analysed for their content of rotigotine. The flux of active substance through skin was calculated by correcting for the influence of the separator membrane.

The diffusion cell described in Tanojo et al. (Tanojo et al. "New design of a flow through permeation cell for in vitro permeation studies across biological membranes" Journal of Controlled Release (1997), 45, 41-47) was used in order to conduct the experiment.

A flask containing the acceptor liquid and the assembled diffusion cells were placed in a temperature-controlled waterbath (32.0±0.5° C.). The acceptor liquid was continuously pumped from the flask through PTFE tubing by a peristaltic pump, passed through the diffusion cells where the diffusion takes place and was then transported via PTFE tubing to test tubes that were placed in a fraction collector.

The required number of disks was punched out from the TDS by using a circular knife. Human epidermis, excised to a thickness of 200-300 μm from fresh donor skin (storage ≦36 hours at 4° C.) with a dermatome (to be referred to as skin) was spread out on laboratory film in petridishes. Using the circular knife the required number of disks was punched out. A disk of membrane was centred on each cell surface. The skin disks were spread out on the membrane disks on the cell surfaces with the aid of forceps. A disk of the TDS is applied to each cell, and the cells were assembled. The experiment was then conducted in a manner similar to the one described in Tanojo et al above.

Afterwards the tubes containing the collected fraction were weighed, and the contents of each tube were analysed using HPLC.

This experiment was carried out for the TDS of Example 1 as well as Comparative Examples 2 and 3.

Figure 6:
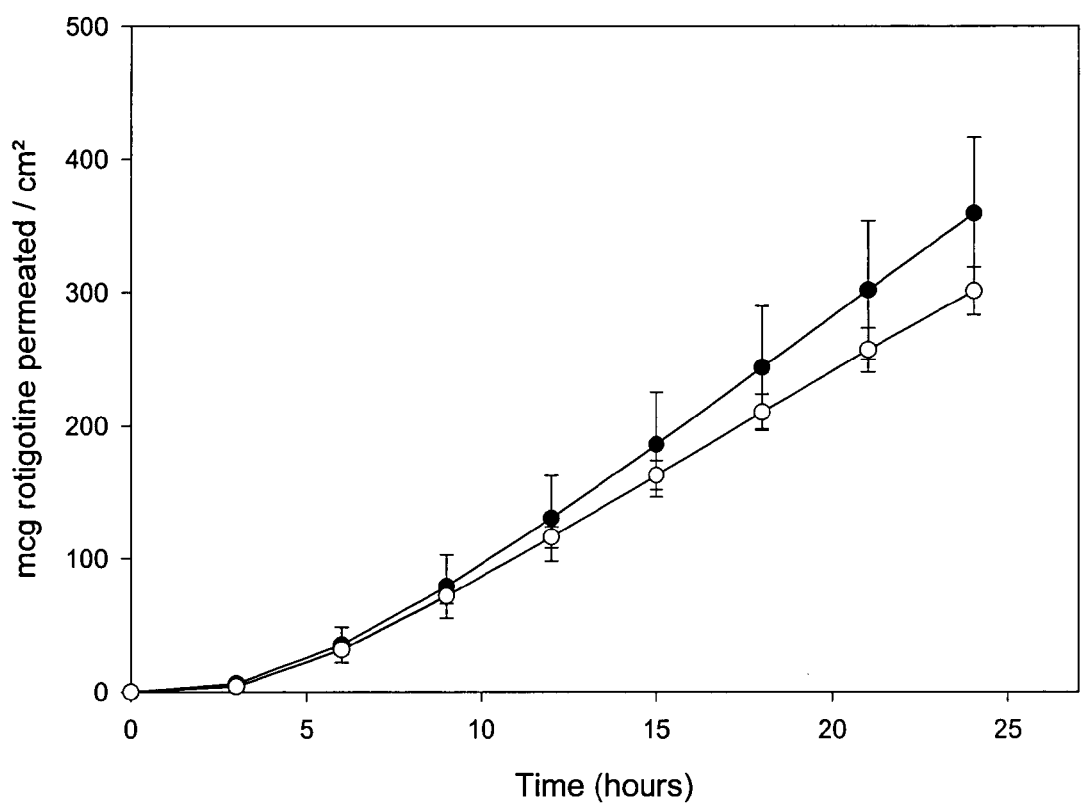
FIG. 6 shows the effect of reducing the amount of the protonated form of the drug in the semi-permeable matrix and reducing the size of the microreservoirs on the in vitro skin permeation of the drug.

FIG. 6 shows the in vitro skin permeation profile for the TDS of Example 1 (●) compared to the TDS of Comparative Example 2 (○).

Figure 7:
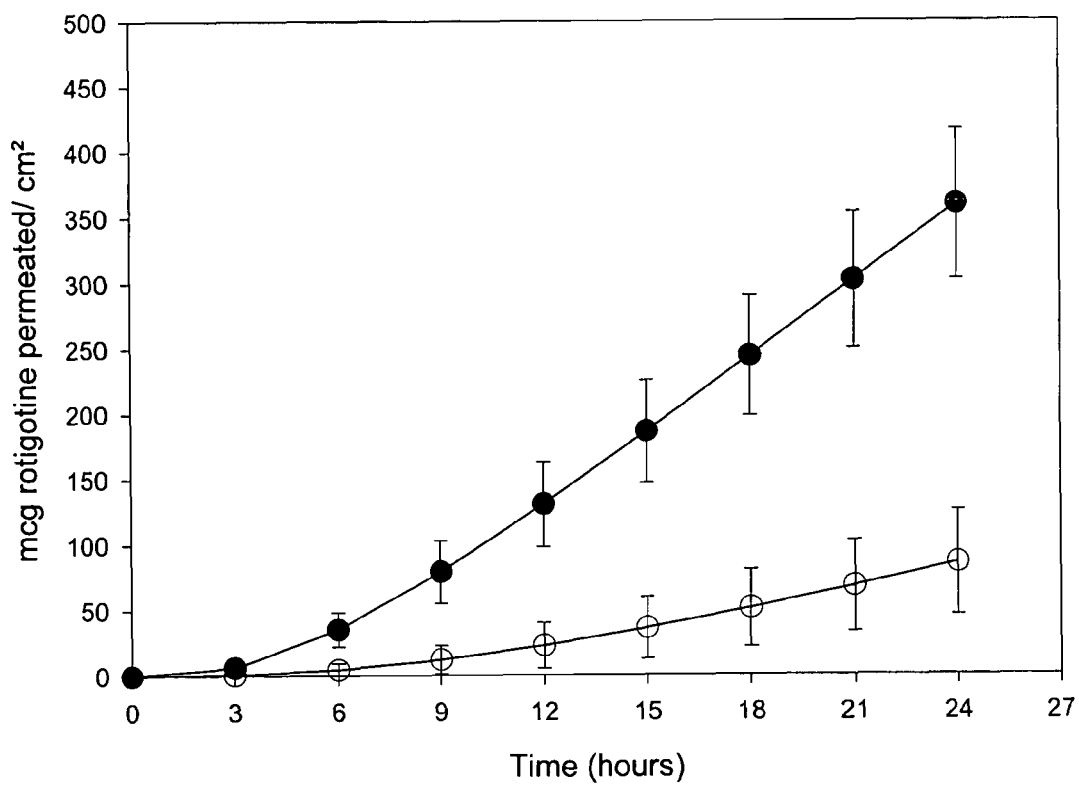
FIG. 7 shows a comparison of the in vitro skin permeation of the drug for the TDS of the, invention and an acrylate-based TDS.

FIG. 7 shows the in vitro skin permeation profile for the TDS of Example 1 (●) compared to the acrylate TDS of Comparative Example 3 (○).

It is clear from the data obtained that the flux across human skin may be significantly enhanced by controlling the size of the microreservoirs in the TDS while at the same time providing a semi-permeable matrix, which is highly permeable for the free base of the amine functional drug while being impermeable for its protonated form.

The invention claimed is:

1. A transdermal delivery system (TDS) comprising
a self-adhesive matrix containing a self-adhesive polymer and microreservoirs containing an amine-functional drug in free base form selected from the group consisting of fentanyl and oxybutynin,
wherein the microreservoirs are within the self-adhesive matrix and have a maximum diameter less than the thickness of the self-adhesive matrix; and
wherein the self-adhesive matrix is permeable to the amine-functional drug in free base form, and the self-adhesive matrix is substantially impermeable to the amine functional drug in protonated form.

2. The TDS of claim 1, wherein the mean diameter of the microreservoirs is in the range of 0.5 to 20 μm.

3. The TDS of claim 1, wherein the self-adhesive matrix is free of silica particles that can absorb salts of the amine functional drug at the TDS/skin interface.

4. The TDS of claim 1, wherein the self-adhesive matrix comprises a silicone pressure sensitive adhesive.

5. The TDS of claim 1, wherein the self-adhesive matrix comprises two or more silicone pressure sensitive adhesives.

6. The TDS of claim 5, wherein the silicone pressure sensitive adhesive is a blend of a high tack silicone pressure sensitive adhesive comprising polysiloxane with a resin and a medium tack silicone pressure sensitive adhesive comprising polysiloxane with a resin.

7. The TDS of claim 1, wherein the microreservoirs further contain at least one crystallization inhibitor comprising soluble polyvinylpyrrolidone, a copolymer of polyvinylpyrrolidone and vinyl acetate, polyethylene glycol, polypropylene glycol, glycerol, a fatty acid ester of glycerol and/or a copolymer of ethylene and vinyl acetate.

8. The TDS of claim 7, wherein the at least one crystallization inhibitor comprises soluble polyvinylpyrrolidone.

9. The TDS of claim 1, wherein the self-adhesive matrix contains $10^3$ to $10^9$ microreservoirs per $cm^2$ of the surface of the matrix.

10. The TDS of claim 1, wherein the maximum diameter of the microreservoirs is not greater than 35 μm.

11. The TDS of claim 1, further comprising a protective foil or sheet to be removed prior to use.

12. The TDS of claim 1, further comprising a backing layer.

13. The TDS of claim 12, wherein the backing layer is inert to the components of the matrix.

14. The TDS of claim 1, wherein the self-adhesive matrix comprises a solid or semisolid semi-permeable polymer.

15. The TDS of claim 1, wherein the self-adhesive matrix contains $10^6$ to $10^9$ microreservoirs per $cm^2$ of the surface of the matrix.

16. The TDS of claim 1, further comprising a backing layer being inert to the component of the matrix, and a protective foil or sheet to be removed prior to use,
wherein the matrix contains $10^3$ to $10^9$ microreservoirs per $cm^2$ of the surface of the matrix, and wherein the maximum diameter of the microreservoirs is less than the thickness of the matrix and is not greater than 35 μm.

17. A transdermal delivery system (TDS) comprising a self-adhesive matrix containing a self-adhesive polymer and microreservoirs containing an amine-functional drug in free base form selected from the group consisting of aminotetralin compounds,
wherein the microreservoirs are within the self-adhesive matrix and have a maximum diameter less than the thickness of the self-adhesive matrix; and
wherein the self-adhesive matrix is permeable to the amine-functional drug in free base form, and the self-adhesive matrix is substantially impermeable to the amine functional drug in protonated form.

* * * * *

UNITED STATES PATENT AND TRADEMARK OFFICE
CERTIFICATE OF CORRECTION

PATENT NO. : 8,246,980 B2
APPLICATION NO. : 10/627990
DATED : August 21, 2012
INVENTOR(S) : Dietrich Wilhelm Schacht, Mike Hannay and Hans-Michael Wolff Page 1 of 1

It is certified that error appears in the above-identified patent and that said Letters Patent is hereby corrected as shown below:

In the Specifications:

Column 6, lines 33-34, replace "(theological)" with --(rheological)--.

Column 8, line 35, replace "Kollidone® 90 F" with --Kollidon® 90F--.

Signed and Sealed this
Third Day of September, 2013

Teresa Stanek Rea
*Acting Director of the United States Patent and Trademark Office*